(12) United States Patent
Inoue et al.

(10) Patent No.: US 8,642,343 B2
(45) Date of Patent: Feb. 4, 2014

(54) BLOOD SEPARATING AGENT AND BLOOD COLLECTION CONTAINER

(75) Inventors: Tomonori Inoue, Shunan (JP); Ryusuke Okamoto, Shunan (JP)

(73) Assignee: Sekisui Medical Co., Ltd., Tokyo (JP)

( * ) Notice: Subject to any disclaimer, the term of this patent is extended or adjusted under 35 U.S.C. 154(b) by 0 days.

(21) Appl. No.: 13/511,944

(22) PCT Filed: Feb. 15, 2011

(86) PCT No.: PCT/JP2011/053139
§ 371 (c)(1),
(2), (4) Date: May 24, 2012

(87) PCT Pub. No.: WO2011/105253
PCT Pub. Date: Sep. 1, 2011

(65) Prior Publication Data
US 2012/0308446 A1    Dec. 6, 2012

(30) Foreign Application Priority Data

Feb. 26, 2010 (JP) .................................. 2010-043142
Aug. 31, 2010 (JP) .................................. 2010-193513

(51) Int. Cl.
*G01N 31/00* (2006.01)

(52) U.S. Cl.
USPC ................ 436/17; 422/430; 422/73; 422/500

(58) Field of Classification Search
USPC ................... 436/17; 422/430, 73, 500
See application file for complete search history.

(56) References Cited

U.S. PATENT DOCUMENTS

| 7,160,849 B2 * | 1/2007 | Tsumori et al. ............... 510/476 |
| 2007/0187341 A1 | 8/2007 | Emerson | |

FOREIGN PATENT DOCUMENTS

| JP | 64-6863 A | 1/1989 |
| JP | 4-175656 A | 6/1992 |
| JP | 9-15238 A | 1/1997 |
| JP | 11-64330 A | 3/1999 |
| JP | 2002-365282 A | 12/2002 |
| JP | 2007-101322 A | 4/2007 |
| JP | 2009-244172 A | 10/2009 |
| WO | WO-2007/029525 A1 | 3/2007 |
| WO | WO-2009/058547 A1 | 5/2009 |

OTHER PUBLICATIONS

International Search Report for the Application No. PCT/JP2011/053139 mailed Mar. 22, 2011.

* cited by examiner

*Primary Examiner* — Monique Cole
(74) *Attorney, Agent, or Firm* — Cheng Law Group, PLLC

(57) ABSTRACT

Provided is a blood separating agent that can form an excellent partition wall in an intermediate layer between clot and serum or between blood cell components and plasma even under low-temperature centrifugation conditions, is less likely to form crevices in the partition wall, is less likely to have any effect on test values, and offers stable performance even after long-term storage. The blood separating agent contains: a polymer for the blood separating agent which is composed of a (meth)acrylic acid ester-based polymer and has a viscosity of 10 to 200 Pa·s at 25° C. and a ratio of viscosity at 15° C. to viscosity at 25° C. of below 4.6; an inorganic powder; and a polyalkylene glycol having a number average molecular weight of 700 or more, wherein the polyalkylene glycol is mixed at a concentration of 5% by weight or less of the total weight of the blood separating agent.

12 Claims, No Drawings

US 8,642,343 B2

BLOOD SEPARATING AGENT AND BLOOD COLLECTION CONTAINER

TECHNICAL FIELD

This invention relates to blood separating agents and blood collection containers for use in separating out serum or plasma from a blood specimen. More particularly, this invention relates to a blood separating agent and a blood collection container which can form a partition wall between clot and serum or between blood cell components and plasma after being centrifuged using differences in specific gravity.

BACKGROUND ART

Previously known blood separating agents of this type include various blood separating agents obtained by adding a specific gravity adjusting agent, a thixotropy enhancer, or a viscosity modifier to a resin. Patent Literature 1 below discloses, as an example of the resin, a mixture of a hydrogenated cyclopentadiene-based petroleum resin solid at ordinary temperature and a plasticizer. Silicone polymers, α-olefin copolymers, acrylic copolymers etc. are also conventionally used.

Examples of the specific gravity adjusting agent used to be added to the resin include inorganic powders, such as silica. On the other hand, examples of the thixotropy enhancer or viscosity modifier for use include various organic compounds. These organic compounds having been heretofore used include glycerin, propylene glycol, ethylene glycol, ethylenediamine, dibenzylidene sorbitol, fatty acid amide, fluorocarbon-based surfactants, polyester-modified alkyl polysiloxane-based surfactants, polyether-modified alkyl polysiloxane-based surfactants, and ethylene glycol-propylene glycol block copolymer-based surfactants.

Furthermore, in using such a hydrogenated cyclopentadiene-based petroleum resin solid at ordinary temperature as exemplified in Patent Literature 1, it is necessary to dissolve the hydrogenated cyclopentadiene-based petroleum resin in a plasticizer to convert it into liquid form at ordinary temperature. Examples of the plasticizer include phthalic acid esters, trimellitic acid esters, sebacic acid esters, and maleic acid esters. However, such a resin component composed of a solid resin and a plasticizer considerably varies in viscosity with temperature owing to the molecular structure of the hydrogenated cyclopentadiene-based petroleum resin, so that the viscosity of the resultant separating agent will be high at low temperatures. Therefore, there arises a problem in that when a cooling centrifuge is used, the fluidity of the blood separating agent will be reduced.

Alternatively, if a silicone polymer is used as the resin, it will react, during long-term storage, with the surfaces of silica particles added as a specific gravity adjusting agent thereto, and consequently the thixotropy of the resultant blood separating agent may be reduced.

On the other hand, in a blood separating agent in which an α-olefin copolymer is used, a large amount of inorganic powder has to be added as a specific gravity adjusting agent because of a small specific gravity of the α-olefin copolymer itself. Therefore, during centrifugation, the inorganic powder may be separated from the resin by a centrifugal force, so that no partition wall may be formed between clot and serum or between blood cell components and plasma. Furthermore, if the amount of inorganic powder added is too large, there arises a problem in that an increase in the hydrogen bonding strength during long-term storage occurs, which in turn increases the viscosity of the resultant separating agent and reduces the fluidity thereof during centrifugation.

If an acrylic copolymer is used, it will generate radicals during sterilization by exposure to γ radiation because of low resistance of the acrylic copolymer itself against exposure to radiation, so that crosslinking caused in the process of progress of the polymerization reaction and the process of main chain breakage and rebinding may increase the viscosity of the acrylic copolymer. Therefore, a satisfactory partition wall may not be able to be formed between clot and serum or between blood cell components and plasma. An example of a method for reducing the increase in viscosity is disclosed in Patent Literature 2 below. In Patent Literature 2, a highly water-soluble polymerization inhibitor, such as hydroquinone, is used. However, if a highly water-soluble polymerization inhibitor is used, the polymerization inhibitor will be eluted from the blood separating agent into serum or plasma. Therefore, there arises a problem in that when the serum or plasma is used as a specimen, its test values will be influenced. In Patent Literature 3, α-methylstyrene dimer serving as a chain transfer agent is added. However, the chain transfer agent presents a problem in that because it has the effect of inhibiting the polymerization in polymer main chains but does not allow radicals to disappear, it is not suited for fundamental reduction of the increase in viscosity.

Furthermore, most of the organic compounds used as thixotropy enhancers or viscosity modifiers are hydrophilic. Therefore, there arises a problem in that the organic compounds are eluted into the blood to damage blood cell membranes. As a result, enzymes and the like contained in large amounts in blood cells, such as LDH and AST, may leak out into plasma or serum. This may have an adverse effect on test values for the plasma or serum. In addition, there is a problem in that absorption of water in blood into the blood separating agent may be promoted to make the blood separating agent cloudy.

Citation List

Patent Literature
  Patent Literature 1: JP-A-H09-15238
  Patent Literature 2: JP-A-H04-175656
  Patent Literature 3: JP-A-2007-101322

SUMMARY OF INVENTION

Technical Problem

An object of the present invention is to provide a blood separating agent that is small in viscosity change due to temperature change, is less likely to elute an organic compound into serum or plasma, can reduce effects on blood cell components, can reliably form a partition wall between clot and serum or between blood cell components and plasma, is less likely to have any effect on test values, and offers stable performance even after long-term storage, and a blood collection container using the blood separating agent.

Solution to Problem

A blood separating agent of the present invention contains a (meth)acrylic acid ester-based polymer having a viscosity of 10 to 200 Pa·s at 25° C. and a ratio of viscosity at 15° C. to viscosity at 25° C. of below 4.6, an inorganic powder, and a polyalkylene glycol having a number average molecular weight (Mn) of 700 or more, wherein the polyalkylene glycol is mixed at a concentration of 5% by weight or less of the total weight of the blood separating agent.

It is desirable that the blood separating agent of the present invention should preferably also contain a polymerization inhibitor having a solubility in water of 4 g/100 mL or below at 25° C.

In the blood separating agent of the present invention, the (meth)acrylic acid ester-based polymer is preferably composed of a copolymer including a (meth)acrylic acid ester monomer and a monomer other than any (meth)acrylic acid ester monomer. The monomer other than any (meth)acrylic acid ester monomer for use is preferably an aromatic vinyl monomer, more preferably styrene or α-methylstyrene.

In the blood separating agent of the present invention, the polyalkylene glycol is preferably a polymer composed of one or more monomers selected from $C_2$ to $C_4$ alkylene oxide monomers and/or a polymer composed of one or more monomers selected from $C_3$ and $C_4$ alkylene oxide monomers.

Furthermore, in the blood separating agent of the present invention, the inorganic powder preferably comprises an inorganic powder having a hydrophilic particle surface, an inorganic powder having a hydrophobic particle surface, or both.

A blood collection container of the present invention includes a container body and the blood separating agent contained in the container body and compounded in accordance with the present invention.

Hereinafter, the present invention will be described in detail.

((Meth)Acrylic Acid Ester-Based Polymer)

In the blood separating agent of the present invention, the polymer for the blood separating agent used is a (meth)acrylic acid ester-based polymer having a viscosity of 10 to 200 Pa·s at 25° C. and a ratio of viscosity at 15° C. to viscosity at 25° C. of below 4.6.

The (meth)acrylic acid ester-based polymer is a principal agent of the blood separating agent for separating clot and serum or separating blood cell components and plasma.

The (meth)acrylic acid ester-based polymer is obtained by polymerizing a raw material containing at least one type of (meth)acrylic acid ester monomer. The raw material may contain a monomer other than any (meth)acrylic acid ester. More specifically, the (meth)acrylic acid ester-based polymer may be a monopolymer of one type of (meth)acrylic acid ester monomer, a copolymer composed of two or more types of (meth)acrylic acid ester monomers, or a copolymer composed of at least one type of (meth)acrylic acid ester monomer and a monomer other than any (meth)acrylic acid ester monomer.

The content of (meth)acrylic acid ester monomer in the (meth)acrylic acid ester-based polymer is preferably 50% to 100% by weight, more preferably 60% to 100% by weight, and still more preferably 70% to 100% by weight. When the content of (meth)acrylic acid ester monomer is 50% by weight or more, the balance among the specific gravity, thixotropy, and fluidity of the polymer for the blood separating agent can be better maintained. Within the above preferred ranges, the balance among them can be made even better.

Examples of the (meth)acrylic acid ester monomer include (meth)acrylic acid alkyl ester containing a $C_1$ to $C_{20}$ alkyl group, (meth)acrylic acid polyalkylene glycol ester, (meth)acrylic acid alkoxyalkyl ester, (meth)acrylic acid hydroxyalkyl ester, (meth)acrylic acid glycidyl ester, (meth)acrylic acid dialkylaminoalkyl ester, (meth)acrylic acid benzyl ester, (meth)acrylic acid phenoxyalkyl ester, (meth)acrylic acid cyclohexyl ester, (meth)acrylic acid isobonyl ester, and (meth)acrylic acid alkoxysilylalkyl ester. One or more of these monomers can be appropriately used as a raw material constituting the (meth)acrylic acid ester-based polymer. Preferably, it is desirable to use two or more of the above (meth)acrylic acid ester monomers. When two or more of the monomers are used, the (meth)acrylic acid ester-based polymer can be easily controlled to have a desired specific gravity and viscosity by adjusting the content ratio between the two or more monomers having different molecular structures.

No particular limitation is placed on the monomer other than any (meth)acrylic acid ester monomer, so long as it is a radical-polymerizable monomer capable of radical copolymerization with (meth)acrylic acid alkyl ester. Examples of such a radical-polymerizable monomer include aromatic vinyl monomers, vinyl esters, vinyl ethers, vinyl pyrrolidones, and (meth)allyl ethers. Examples of the aromatic vinyl monomers include styrene, α-methylstyrene, p-methylstyrene, α-methyl-p-methylstyrene, p-methoxystyrene, o-methoxystyrene, 2,4-dimethylstyrene, chlorostyrene, and bromostyrene. Examples of the vinyl esters include (meth)acrylate, maleic anhydride, fumarate, (meth)acrylamide, dialkyl(meth)acrylamide, and vinyl acetate. One or more of these radical-polymerizable monomers can be appropriately used.

The radical-polymerizable monomer is preferably an aromatic vinyl monomer, more preferably styrene or α-methylstyrene. Aromatic vinyl monomers have large specific gravity and high hydrophobicity and are therefore effective in reducing the adsorption of drugs while ensuring the blood separation capability of the blood separating agent. Furthermore, the resultant copolymer obtained by copolymerization of such an aromatic vinyl monomer and a (meth)acrylic acid ester is less likely to increase the molecular weight and the viscosity during sterilization by radiation, as compared with (meth)acrylic acid ester-based polymers containing no aromatic vinyl monomer.

The content of aromatic vinyl monomer in the monomer composition for obtaining the (meth)acrylic acid ester-based polymer is preferably not less than 1% by weight and less than 50% by weight, more preferably within the range of 5% to 30% by weight, and still more preferably within the range of 10% to 20% by weight. If the content of aromatic vinyl monomer is less than 1% by weight, the effect due to the use of aromatic vinyl monomer cannot be satisfactorily achieved. On the other hand, if the content of aromatic vinyl monomer is 50% by weight or more, the viscosity of the polymer for the blood separating agent will be too high, which may make it difficult to ensure adequate fluidity.

The (meth)acrylic acid ester-based polymer can be obtained by an ordinary radical polymerization process. Examples of the radical polymerization process include a solution polymerization process, a bulk polymerization process, a dispersion polymerization process, and a living radical polymerization process.

In order to form a partition wall in an intermediate layer between clot (specific gravity: 1.08) and serum (specific gravity: 1.03) or between blood cell components (specific gravity: 1.08) and plasma (specific gravity: 1.03), the specific gravity of the blood separating agent is preferably 1.035 to 1.060. Therefore, the specific gravity of the (meth)acrylic acid ester-based polymer at 25° C. is preferably 1.025 to 1.060 and more preferably 1.030 to 1.050. If the specific gravity thereof is below 1.025, it will be necessary to add a large amount of inorganic powder in order to adjust the specific gravity of the blood separating agent to within the above range. As a result, the inorganic powder and the polymer for the blood separating agent will be separated from each other by centrifugation or the blood separating agent will absorb moisture during long-term storage. Thus, the hydrogen bonding strength between the inorganic powder particles will increase, which may reduce the fluidity of the blood separating agent. Consequently, there may arise a problem in that a partition wall cannot be formed in an intermediate layer between clot and serum or between blood cell components and plasma. On the other hand, if the specific gravity is above 1.060, the addition of inorganic powder necessary to give thixotropy to the polymer for the blood separating agent will make the specific gravity of the blood separating agent excessively high, so that a partition wall may not be able to be formed in an intermediate layer between clot and serum or between blood cell components and plasma.

The weight-average molecular weight (Mw) of the (meth) acrylic acid ester-based polymer is preferably within the range of 3000 to 50000 and more preferably within the range of 4000 to 30000. When the weight-average molecular weight is within the above ranges, the fluidity of the blood separating agent can be well maintained and the strength of the resultant partition wall formed can be increased. If the weight-average molecular weight is below 3000, the strength of the partition wall may be insufficient. Or suspended matter may form in serum or plasma to have an adverse effect on test values or contaminate sensitive analytical equipment. If the weight-average molecular weight is above 50000, the fluidity during centrifugation will be reduced, so that a partition wall may not be able to be reliably formed between clot and serum or between blood cell components and plasma.

The viscosity of the (meth)acrylic acid ester-based polymer at 25° C. is 10 to 200 Pa·s and preferably 30 to 150 Pa·s. When the viscosity is within the above ranges, the fluidity of the blood separating agent can be increased to ensure the strength of the resultant partition wall. If the viscosity is below 10 Pa·s, the strength of the partition wall may be insufficient or suspended matter may form in serum or plasma to have an adverse effect on test values or contaminate sensitive analytical equipment. If the viscosity at 25° C. is above 200 Pa·s, the fluidity during centrifugation will be reduced, so that a partition wall will not be able to be reliably formed between clot and serum or between blood cell components and plasma.

Furthermore, the ratio of the viscosity of the (meth)acrylic acid ester-based polymer at 15° C. to the viscosity thereof at 25° C. ((viscosity at 15° C.)/(viscosity at 25° C.)) is below 4.6, preferably not less than 1 and less than 4.6. If the above viscosity ratio is 4.6 or more, the change in viscosity of the blood separating agent may be too large under centrifugation conditions at low temperatures, such as at 15° C. or below. Therefore, the fluidity will be reduced, so that a partition wall will not be able to be reliably formed between clot and serum or between blood cell components and plasma. In addition, generally, the liquid viscosity changes with temperature; the lower the temperature, the higher the viscosity. Therefore, if the above viscosity ratio is 1, this means that there is no change in viscosity depending on temperature. Hence, it is desirable to have the viscosity ratio as close to 1 as possible.

(Polymerization Inhibitor)

The polymerization inhibitor is a compound having the effect of reacting with an active radical species which may cause radical polymerization, thereby turning it into an inactive radical or stable compound which does not cause radical polymerization.

In the present invention, the polymerization inhibitor that can be added to the polymer for the blood separating agent preferably has a solubility in water of 4 g/100 mL or below at 25° C. More preferably, it is desirable to use a polymerization inhibitor of extremely small solubility in water. If the solubility in water at 25° C. is higher than 4 g/100 mL, the polymerization inhibitor will likely be eluted into serum or plasma located on top of the partition wall after centrifugation. If the polymerization inhibitor is eluted into serum or plasma, this may have an influence on the measurement results for items measured with a measuring reagent using redox reaction. Furthermore, certain polymerization inhibitors may produce color when eluted, which may have an influence on a measurement results for items relating to the degree of coloration, or the like. Therefore, it is preferred that the polymer for the blood separating agent should not contain any polymerization inhibitor of which solubility in water at 25° C. is above 4 g/100 mL.

No particular limitation is placed on the type of the polymerization inhibitor so long as, for example, the solubility in water at 25° C. is 4 g/100 mL or below. Examples of such a polymerization inhibitor include hydroxy aromatic compounds, hydroquinone compounds, and quinone compounds; such as p-methoxyphenol, benzoquinone, cresol, t-butylcatechol, t-butylhydroquinone, 2,5-di-t-butylhydroquinone, p-nitrosophenol, and 3,5-di-t-butyl-4-hydroxytoluene. Furthermore, examples thereof also include sulfur compounds, such as 4,4'-thiobis(3-methyl-6-t-butylphenol) and phenothiazine; amine compounds, such as diphenylamine and cupferron; copper salt compounds, and manganese salt compounds.

Although no particular limitation is placed on the amount of polymerization inhibitor added so long as it is within the range in which the increase in viscosity of the blood separating agent due to exposure to radiation can be reduced and there is no effect on test values to be described later, it is preferably 0.001% to 5% by weight per 100% by weight of blood separating agent. More preferably, the amount of polymerization inhibitor added is 0.005% to 3% by weight. If the above amount is less than 0.001% by weight, the increase in viscosity of the blood separating agent due to exposure to radiation cannot be reduced enough, which may impair the formation of a partition wall after centrifugation. On the other hand, if more than 5% by weight of polymerization inhibitor is added, the inhibitor may not be fully dispersed in the polymer for the blood separating agent, so that it may remain in the form of granular aggregates in the polymer for the blood separating agent.

No particular limitation is placed on the method for adding the polymerization inhibitor; examples of the method include direct addition of a powdered or liquid polymerization inhibitor to the (meth)acrylic acid ester-based polymer and addition of a polymerization inhibitor dissolved in an organic solvent to the (meth)acrylic acid ester-based polymer.

(Inorganic Powder)

In the present invention, the inorganic powder is used as a specific gravity adjusting agent. No particular limitation is placed on the type of the inorganic powder; examples of the inorganic powder that can be used are silicon dioxide-based inorganic powders, such as clay minerals made of silica, bentonite, smectite, or the like.

Furthermore, in the present invention, the particle surface of the inorganic powder may have hydrophilicity or hydrophobicity. Alternatively, an inorganic powder having a hydrophobic particle surface and an inorganic powder having a hydrophilic particle surface may be used in combination.

By adding the above inorganic powder, preferably a silicon dioxide-based powder, to the polymer for the blood separating agent described above, the blood separating agent can be given thixotropy.

Because silicon dioxide-based powders have hydroxy groups on their particle surface, they exhibit hydrophilicity. Furthermore, when the hydroxy groups on the particle surface are substituted by methyl groups or the like, the silicon dioxide-based powders can be appropriately given hydrophobicity.

Note that whether the inorganic powder is hydrophilic or hydrophobic is generally determined by the state of the inorganic powder upon dispersion into a water-alcohol mixture solvent. If hydroxy groups are present on the particle surface of the inorganic powder and the inorganic powder can be dispersed into pure water, it is determined that hydroxy groups remain intact on the particle surface and the inorganic powder is hydrophilic.

On the other hand, if the inorganic powder can be dispersed only into water-alcohol mixture solvents, it is an inorganic powder whose particle surface is hydrophobic. The alcohol that can be used is methanol or ethanol. Hydrophobic inorganic powders that are easy to use are those having a hydrophobicity to such an extent that they can be dispersed into a water-alcohol mixture solvent having an alcohol concentration of 25% by volume or more. In fact, commonly available hydrophobic inorganic powders are those in which some of hydroxy groups on the particle surface of a hydrophilic inorganic powder are substituted or blocked with alkylsilyl groups, such as dimethylsilyl groups, trimethylsilyl groups, octylsilyl groups, silicone oil, or the like.

In the present invention, a silicon dioxide-based powder is suitably used as the inorganic powder because it has no catalytic activity that decomposes organic substances, such as liquid resin, and therefore will not have an adverse effect on test values. Among silicon dioxide-based inorganic powders, hydrophilic silicas available and easy to use are those produced by gas-phase processes, such as AEROSIL series (manufactured by Nippon Aerosil Co., Ltd.) including AEROSIL 90G, 130, 200, and 300, REOLOSIL series (manufactured by Tokuyama Corporation) including REOLOSIL QS-10, QS-20, and QS-30, and WACKER HDK series (manufactured by Wacker Asahikasei Silicone Co., Ltd.) including WACKER HDK S13, N20, and T30.

Hydrophobic silicas available and easy to use are those produced by gas-phase processes, such as AEROSIL series (manufactured by Nippon Aerosil Co., Ltd.) including AEROSIL R972, R974, R805, and R812, REOLOSIL series (manufactured by Tokuyama Corporation) including REOLOSIL MT-10, DM-30S, HM-30S, KS-20S, and PM-20, and WACKER HDK series (manufactured by Wacker Asahikasei Silicone Co., Ltd.) including WACKER HDK H15, H18, and H30.

The inorganic powder is preferably a fine powder. The reason for this is that in comparison between different powders of different particle sizes to be added in equal proportions to their respective blood separating agents, the finer powder having a larger specific surface area and a smaller average particle size can increase the capability of imparting thixotropy and the effect of controlling the viscosity to a greater extent. In this case, the average size of primary particles of the fine powder is preferably 1 to 100 μm and more preferably 5 to 50 μm. If the average size of primary particles is below 1 μm or above 100 μm, this will make it difficult to adjust the thixotropy of the blood separating agent to a suitable level. The specific surface area of the fine powder is preferably 10 to 1000 m$^2$/g and more preferably 50 to 500 m$^2$/g. If the specific surface area is below 10 m$^2$/g or above 1000 m$^2$/g, this will make it difficult to suitably control the thixotropy of the blood separating agent.

The proportion of the inorganic powder mixed in the blood separating agent is preferably within the range of 0.5% to 5% by weight, more preferably 1% to 4% by weight, per 100% by weight of the blood separating agent. If the proportion thereof is below 0.5% by weight, a satisfactory thixotropy may not be exhibited. If the proportion is above 5% by weight, the specific gravity will be increased, which will reduce the fluidity of the blood separating agent.

(Polyalkylene Glycol)

The above polyalkylene glycol is used as a thixotropy enhancer. The polyalkylene glycol is a polymer composed of one or more monomers selected from $C_2$ to $C_4$ alkylene oxide monomers and/or a polymer composed of one or more monomers selected from $C_3$ and $C_4$ alkylene oxide monomers, and its number average molecular weight is 700 or more. By adding the polyalkylene glycol to the polymer for the blood separating agent described above, the thixotropy of the blood separating agent can be enhanced.

In the blood separating agent according to the present invention, each of the polyalkylene glycols specified above may be used singularly, or two or more types of them may be combined.

If the molecule of the polyalkylene glycol excessively contains a polymerization component of a $C_2$ ethylene glycol monomer, this increases the water solubility and therefore is not preferred. Hence, the preferred polyalkylene glycols for use are those having an HLB value of 16 or less as calculated by the Davies method. The HLB value by the Davies method is calculated from the following equation.

<($HLB$ value)=7+(sum of hydrophilic group numbers)−(sum of lipophilic group numbers)>

The group number refers to a specific numerical value assigned to each functional group.

Furthermore, either or both of a polyalkylene glycol having a single hydroxy group per molecule and a polyalkylene glycol having more than one hydroxy groups per molecule can be used depending on the number of hydroxy groups derived from the number of functional groups of alcohol as a starting material or depending on whether the treatment for blocking the hydroxy groups with alkyl groups or the like has been performed or not. In order to reduce the water solubility, the number of hydroxy groups per molecule is preferably three or less.

The molecule of the polyalkylene glycol may contain a hydrophobic residue introduced for a purpose other than blocking of hydroxy groups. Examples of such a hydrophobic residue include alkylene groups, alkene groups, alkyne groups, aromatic ring groups, and dimethylsiloxane substituents.

Furthermore, the polyalkylene glycol may contain, instead of or in addition to the hydroxy groups, hydrogen-bonding polar groups, such as carbonyl groups, amino groups, or thiol groups. Also in this case, the number of polar groups per molecule is preferably three or less in order to reduce the water solubility.

If the number average molecular weight of the polyalkylene glycol is smaller than 700, crevices will form in a partition wall formed after centrifugation. As a result, clot and serum will be mixed or blood cell components and plasma will be mixed to have an adverse effect on test values. Therefore, the number average molecular weight should be at least 700. Preferably, when a polyalkylene glycol having two or more hydroxy groups is used, it is desirable that the number average molecular weight should be at least 1000. In this case, the water solubility can be further reduced and the adverse effect on blood test values can be further reduced. Although no particular limitation is placed on the upper limit of the number average molecular weight of the polyalkylene glycol, it is preferably at most 100,000. If the number average molecular weight thereof is above 100,000, the hydroxy group density will be low, so that the polyalkylene glycol may not act as a thixotropy enhancer.

The concentration of the polyalkylene glycol should be 5% by weight or less of the total weight of the blood separating agent. When the concentration thereof is 5% by weight or less, the blood separating agent can be controlled within a favorable viscosity range and the adverse effect on test values can be reduced. The concentration is preferably at most 3% by weight, and more preferably at most 2% by weight. On the other hand, the preferred lower limit of the concentration of the polyalkylene glycol is 0.1% by weight. When the concentration is 0.1% by weight or more, the viscosity range of the blood separating agent can be controlled within a favorable range.

Specific examples of the polyalkylene glycol specified above include the following various types of polyalkylene glycols. However, the polyalkylene glycol for use is not limited to the materials exemplified below.

Examples of polyalkylene glycols having more than one terminal hydroxy group include polybutylene glycols (UNIOL PB series manufactured by NOF Corporation, such as PB-700, PB-1000, and PB-2000), polypropylene glycols (UNIOL D series manufactured by NOF Corporation, such as D-700, D-1200, and D-4000), polyoxypropylene glyceryl ethers (UNIOL TG series manufactured by NOF Corporation, such as TG-1000, TG-3000, and TG-4000), polyoxypropylene sorbit (UNIOL HS series manufactured by NOF Corporation, such as HS-1600D), POLYCERIN (manufactured by NOF Corporation, including POLYCERIN DCB series, such as DCB-1000, DCB-2000, and DCB-4000, and POLYCERIN DC series, such as DC-1100, DC-1800E, and DC-3000E), polyoxypropylene diglyceryl ethers (UNILUBE series manufactured by NOF Corporation, such as DCP-700), polyoxypropylene glyceryl ethers (PREMINOL series manufactured by Asahi Glass Co., Ltd., such as S3003, S3006, and S3011), polypropylene glycols (PREMINOL series manufactured by Asahi Glass Co., Ltd., such as S4001, S4006, S4011, and S4015), polyoxyethylene-polyoxypropylene glycols (NEWPOL PE series manufactured by Sanyo Chemical Industries, Ltd., such as PE-34, PE-61, PE-62, PE-64, PE-71, and PE-74), and polyoxyethylene-polyoxypropylene glyceryl ethers (ADEKA polyethers manufactured by ADEKA Corporation, such as AM-502).

Examples of polyalkylene glycols having a single terminal hydroxy group include polyoxypropylene butyl ethers (UNILUBE MB series manufactured by NOF Corporation, such as MB-7, MB-14, MB-38, and MB-700), polyoxypropylene glycol monoethers (NEWPOL LB series manufactured by Sanyo Chemical Industries, Ltd., such as LB-285, LB-625, LB-3000, and LB-1800×), and polyoxypropylene alkyl ethers (PREMINOL series manufactured by Asahi Glass Co., Ltd., such as S1004F and S1005).

(Water)

In the blood separating agent according to the present invention, water may be added thereto in order to increase the thixotropy. Water is coordinated at hydroxy groups on the particle surface of the inorganic powder and promotes the formation of a network of hydrogen bonding via hydroxy groups between adjacent inorganic powder particles. Thus, the necessary amount of inorganic powder can be reduced. In other words, the concentration of inorganic powder in the blood separating agent can be reduced.

In respect of use of water, deionized water, such as distilled water or ion-exchange water, can be appropriately used. Furthermore, water is preferably used at a concentration necessary to coordinate a single water molecule at each hydroxy group on the particle surface of the inorganic powder or higher concentrations.

In the blood separating agent according to the present invention, additives, such as a compatibilizing agent or an antioxidant, may be further added thereto within the range in which the performance as a blood separating agent can be maintained.

(Production Method)

No particular limitation is placed on the method for producing the blood separating agent according to the present invention. For example, the (meth)acrylic acid ester-based polymer, the inorganic powder, and the polyalkylene glycol specified above only have to be mixed together by an appropriate process. The mixing process is not particularly limited and examples thereof include processes using any known mixer, such as a planetary mixer, a roll mil, or a homogenizer.

(Blood Collection Container)

The blood collection container according to the present invention includes a container body and the blood separating agent contained in the container body and according to the present invention. No particular limitation is placed on the type of the container body, and container bodies that can be used include bottomed cylindrical containers commonly used as blood collection tubes and various centrifugable cylindrical containers. No particular limitation is also placed on the material of the body so long as it can withstand centrifugation, and materials thereof that can be used include synthetic resins and glasses.

No particular limitation is also placed on the manner to contain the blood separating agent in the container body. For example, a method of containing the liquid blood separating agent in a container body having a bottomed cylindrical shape can be used as appropriate.

Advantageous Effects of Invention

Since the blood separating agent according to the present invention contains the specified (meth)acrylic acid ester-based polymer, the inorganic powder, and the specified polyalkylene glycol, wherein the polyalkylene glycol is mixed at a concentration of 5% by weight or less of the total weight of the blood separating agent; the fluidity of the blood separating agent is less likely to be reduced even during centrifugation under low-temperature centrifugation conditions as with the use of a cooling centrifuge. Therefore, a partition wall can be reliably formed in an intermediate layer between clot and serum or between blood cell components and plasma.

In addition, since the specified polyalkylene glycol, which is less likely to cause components of the blood separating agent to be eluted into serum or plasma and less likely to have an adverse effect on blood cell components, is added as a thixotropy enhancer, it can be avoided that the polymer for the blood separating agent is broken during centrifugation, oil drops drift in the blood, and oil films float on the blood surface. Therefore, the reaction cell or the surface of the electrolyte measurement electrode of an analyzer is less likely to be contaminated and is less likely to present the problem of inducing measurement errors. Furthermore, since the amount of inorganic powder added can be reduced, this makes it difficult to cause a reduction in fluidity due to increase in hydrogen bonding during long-term storage.

DESCRIPTION OF EMBODIMENTS

Hereinafter, the present invention will become apparent by reference to specific examples of the invention and comparative examples. Note that the present invention is not limited to the following examples.

EXAMPLES 1 TO 8 AND COMPARATIVE EXAMPLES 1 TO 7

(Materials Used in Examples 1 to 8 and Comparative Examples 1 to 7)

1) Polymer for Blood Separating Agent

Materials used as polymers for blood separating agents are shown in Table 1 below.

TABLE 1

|  |  | Mw | Specific Gravity | Styrene Contained | Viscosity at 25° C. (Pa·s) | 15° C./25° C. Viscosity Ratio | Viscosity at 25° C. After Exposure to γ Radiation |
|---|---|---|---|---|---|---|---|
| Polymer 1 | (Meth) acrylic acid | 5100 | 1.030 | Yes | 25 | 3.1 | 34 |
| Polymer 2 | ester polymer | 5800 | 1.031 | Yes | 65 | 3.3 | 88 |
| Polymer 3 | (manufactured by | 7600 | 1.031 | Yes | 90 | 3.8 | 123 |
| Polymer 4 | Toagosei Co., Ltd.) | 25000 | 1.033 | No | 70 | 2.7 | 142 |
| Polymer 5 |  | 2900 | 1.032 | Yes | 6 | 2.7 | 8 |
| Polymer 6 | Fused mixture of hydrogenated cyclopentadiene-based solid resin and trimellitic acid ester |  | 1.033 | No | 65 | 4.6 | 68 |

The 15° C./25° C. Viscosity Ratio refers to the ratio of viscosity at 15° C. to viscosity at 25° C. The Viscosity at 25° C. After Exposure to γ Radiation refers to the viscosity at 25° C. after the polymer is exposed to γ radiation at an average dose of 30 kGy. The measurement of viscosity was performed with a rheometer DV-III (manufactured by Brookfield Engineering Laboratories, Inc.).

2) Inorganic Powder

The inorganic powder used was a mixture of a hydrophilic silica (AEROSIL 200 manufactured by Nippon Aerosil Co., Ltd., particle size: approx. 12 nm, specific surface area: approx. 200 m$^2$/g) and a hydrophobic silica (AEROSIL R974 manufactured by Nippon Aerosil Co., Ltd., particle size: approx. 12 nm, specific surface area: approx. 170 m$^2$/g, which was made hydrophobic by chemically treating the particle surface with CH$_3$ groups). The mixture ratio was (hydrophilic silica)/(hydrophobic silica)=0.68 (by weight).

3) Polyalkylene Glycol

Polyalkylene glycols indicated by Thixotropy Enhancers 1 to 4 shown in Table 2 below were prepared as polyalkylene glycols.

Enhancer 1: polyoxypropylene glyceryl ether (PREMINOL S3011 manufactured by Asahi Glass Co., Ltd.)

Enhancer 2: polyoxyethylene-polyoxypropylene glycol (NEWPOL PE-74 manufactured by Sanyo Chemical Industries, Ltd.)

Enhancer 3: polybutylene glycol (UNIOL PB-700 manufactured by NOF Corporation)

Enhancer 4: polyoxypropylene glyceryl ether (ADEKA polyether G300 manufactured by ADEKA Corporation)

TABLE 2

|  | Material Name | Trade Name | Mn | HLB (Davies Method) |
|---|---|---|---|---|
| Enhancer 1 | Polyoxypropylene glyceryl ether | PREMINOL S3011 | 10,000 | −13 |
| Enhancer 2 | Polyoxyethylene-polyoxypropylene glycol | NEWPOL PE-74 | 3,417 | 12 |
| Enhancer 3 | Polybutylene glycol | UNIOL PB-700 | 700 | 5 |
| Enhancer 4 | Polyoxypropylene glyceryl ether | ADEKA Polyether G300 | 350 | 12 |

(Preparation of Blood Separating Agent)

EXAMPLE 1

A blood separating agent was prepared by making a formulation containing 96% by weight of Polymer 1 shown as a polymer for a blood separating agent in Table 1, 3% by weight of inorganic powder which is the above-described mixture, and 1% by weight of Thixotropy Enhancer 1 shown as a polyalkylene glycol in Table 2, followed by mixing with stirring at room temperature using a planetary mixer.

EXAMPLES 2 TO 8 AND COMPARATIVE EXAMPLES 1 TO 7

Blood separating agents were prepared in the same manner as in Example 1, except that the materials used and the mixture ratio thereof were varied as shown in Table 3 below. In Comparative Example 1, no inorganic powder was used. In Comparative Example 2, no polyalkylene glycol was used. In Comparative Example 3, Polymer 5 for a blood separating agent having a low viscosity was used. In Comparative Example 4, Polymer 5 for a blood separating agent was used and the amount of inorganic powder added was 5% by weight. In Comparative Example 5, a fused mixture of a hydrogenated cyclopentadiene-based solid resin and a trimellitic acid ester was used as a polymer for a blood separating agent. In Comparative Example 6, the amount of Thixotropy Enhancer 1 added was 10% by weight. In Comparative Example 7, Thixotropy Enhancer 4 having a number average molecular weight of 350 was used.

TABLE 3

|  | Polymer for Blood Separating Agent | | Inorganic Fine Powder | Polyalkylene Glycol | |
|---|---|---|---|---|---|
|  | Type | % by weight | % by weight | Type | % by weight |
| Ex. 1 | Polymer 1 | 96 | 3 | Enhancer 1 | 1 |
| Ex. 2 | Polymer 2 | 96.9 | 3 | Enhancer 1 | 0.1 |
| Ex. 3 | Polymer 2 | 96 | 3 | Enhancer 1 | 1 |
| Ex. 4 | Polymer 2 | 92 | 3 | Enhancer 1 | 5 |
| Ex. 5 | Polymer 2 | 96 | 3 | Enhancer 2 | 1 |
| Ex. 6 | Polymer 2 | 96 | 3 | Enhancer 3 | 1 |
| Ex. 7 | Polymer 3 | 96 | 3 | Enhancer 1 | 1 |
| Ex. 8 | Polymer 4 | 96 | 3 | Enhancer 1 | 1 |
| Comp. Ex. 1 | Polymer 2 | 99 | — | Enhancer 1 | 1 |
| Comp. Ex. 2 | Polymer 2 | 97 | 3 | — | — |
| Comp. Ex. 3 | Polymer 5 | 96 | 3 | Enhancer 1 | 1 |
| Comp. Ex. 4 | Polymer 5 | 94 | 5 | Enhancer 1 | 1 |
| Comp. Ex. 5 | Polymer 6 | 96 | 3 | Enhancer 1 | 1 |
| Comp. Ex. 6 | Polymer 2 | 87 | 3 | Enhancer 1 | 10 |
| Comp. Ex. 7 | Polymer 2 | 96 | 3 | Enhancer 4 | 1 |

(Preparation of Blood Collection Container)

Ten 10-mL polyethylene terephthalate-made test tubes (16 mm diameter by 100 mm length) were prepared and each of the blood separating agents of Examples 1 to 8 and Comparative Examples 1 to 7 was contained in the ten test tubes, approximately 1.2 g per test tube, to prepare blood collection containers. Furthermore, twenty 7-mL polyethylene terephthalate-made test tubes (13 mm diameter by 100 mm length) were prepared and each of the blood separating agents of Examples 1 to 8 and Comparative Examples 1 to 7 was contained in the twenty test tubes, 0.9 g per test tube, to prepare blood collection containers. The blood collection containers prepared using 7-mL polyethylene terephthalate-made test tubes were exposed to γ radiation to reach a dose of 30 kGy and then evaluated in various items.

(Evaluations)

Just after preparation of the blood collection containers in the above manner, samples of the blood separating agents and blood collection containers were subjected to an accelerated test corresponding to the degree of storage at 25° C. for one year, and evaluated in the following manners. Furthermore, samples thereof subjected to an accelerated test corresponding to the degree of storage at 25° C. for one year were also evaluated in the following manners. The accelerated test was conducted by storing the samples for four weeks under conditions of a temperature of 45° C. and a relative humidity of 75%.

1) Fluidity Evaluation of Blood Separating Agent

Ten of the 7-mL blood testing containers were filled with 2 mL of brine controlled to a specific gravity of 1.08, and the ten blood collection containers were immersed into a water bath set at 15° C. for 30 minutes. Thirty minutes after, the blood collection containers were subjected to centrifugation using a cooling centrifuge under conditions of 1100 g for five minutes at 15° C. When a partition wall having an average thickness of 5 mm or more was formed above the brine having a specific gravity of 1.08, this result is indicated by a circle sign. When the average thickness of a partition wall formed was not less than 2 mm and less than 5 mm, this result is indicated by a triangle sign. When the average thickness of a partition wall formed was less than 2 mm, this result is indicated by a cross sign. These results are indicated in Table 4 below.

2) Fluidity Resistance Evaluation

Five of the 10-mL blood collection containers were held in horizontal positions at 60° C. for 24 hours, the separating agent compositions were measured in terms of their respective moving distances from the initial liquid levels to the leading ends in 24 hours, and the average of the measured values was calculated. This evaluation was made only of the samples just after preparation of the blood collection containers.

3) Evaluation of Formation State of Partition Wall

Citrate phosphate dextrose adenine (CPDA-1) added human preserved blood (available from Tennessee Blood Services) was prepared. An amount of 5 mL of the above human preserved blood was contained in each of five of the 7-mL blood collection containers containing the blood separating agent of each example and mixed with the blood separating agent by turning the container upside down, and the mixture was then centrifuged under conditions of 2200 g for five minutes at 20° C. Then, visual inspection was made of the separating state of plasma and blood cell components due to the partition wall formed after centrifugation and the presence or absence of oily suspended matter and oil film. The results are shown in Table 4 below. In Table 4, the occurrence of crevices in the partition wall is indicated by "crevice", the formation of oily suspended matter or oil film is indicated by "oil", and no observation of these phenomena is indicated by a circle sign.

TABLE 4

| | Fluidity (1100 g × 5 min/ 15° C.) | | Fluidity Resistance | Formation State of Partition Wall | |
|---|---|---|---|---|---|
| | Initial | After accelerated test | (mm) Just after preparation | Initial | After accelerated test |
| Ex. 1 | ○ | ○ | 6.3 | ○ | ○ |
| Ex. 2 | ○ | ○ | 6.8 | ○ | ○ |
| Ex. 3 | ○ | ○ | 3.7 | ○ | ○ |
| Ex. 4 | ○ | ○ | 6.5 | ○ | ○ |
| Ex. 5 | ○ | ○ | 2.8 | ○ | ○ |
| Ex. 6 | ○ | ○ | 5.1 | ○ | ○ |
| Ex. 7 | ○ | ○ | 3.3 | ○ | ○ |
| Ex. 8 | ○ | △ | 3.6 | ○ | ○ |
| Comp. Ex. 1 | ○ | ○ | 90 mm or more | oil | oil |
| Comp. Ex. 2 | ○ | ○ | 90 mm or more | crevice, oil | crevice, oil |
| Comp. Ex. 3 | ○ | ○ | 90 mm or more | oil | oil |
| Comp. Ex. 4 | x | x | 1.2 | ○ | oil |
| Comp. Ex. 5 | △ | x | 2.7 | ○ | ○ |
| Comp. Ex. 6 | ○ | ○ | 32.6 | oil | oil |
| Comp. Ex. 7 | ○ | ○ | 8.2 | crevice | crevice |

As is evident from Table 4, Examples 1 to 8 exhibited good results in terms of all of the fluidity, the fluidity resistance, and the formation state of partition wall even after the accelerated test.

In Comparative Example 1 in which no inorganic powder was added, Comparative Example 2 in which no polyalkylene glycol was added, and Comparative Example 3 in which the viscosity of the polymer for the blood separating agent was low, sufficient thixotropy was not achieved so that the blood separating agents flowed out to the openings of the test tubes. In addition, oily suspended matter or oil films were formed after centrifugation.

As compared with Comparative Example 3 that exhibited low viscosity and insufficient thixotropy, Comparative Example 4 having enhanced thixotropy by the addition of 5% by weight of inorganic powder exhibited reduced fluidity, so that a satisfactory partition wall was not be able to be formed.

In Comparative Example 5 in which the polymer for the blood separating agent composed of a solid resin and a plasticizer was used, a high temperature dependency of its viscosity reduced the fluidity of the resultant blood separating agent, so that a partition wall was not be able to be formed satisfactorily.

In Comparative Example 6 in which 10% by weight of polyalkylene glycol was added, the blood separating agent flowed and oily suspended matter or oil films were formed after centrifugation, probably because of reduction in viscosity of the blood separating agent due to the excessive addition of low-viscosity polyalkylene glycol.

In Comparative Example 2 in which no polyalkylene glycol was added and Comparative Example 7 in which a polyalkylene glycol having a number average molecular weight of 350 was used, crevices were formed in the partition walls after centrifugation.

In contrast, in all of Examples 1 to 8, partition walls having sufficient thicknesses could be formed with certainty after centrifugation. In addition, it was confirmed that even when the blood separating agents were subjected to the accelerated test corresponding to storage at 25° C. for one year, they offered stable performance.

EXAMPLES 9 TO 27 AND COMPARATIVE EXAMPLES 8 TO 13

A description is given of Examples 9 to 27 and Comparative Examples 8 to 13 in all of which a polymerization inhibitor was added.

<Materials Used in Examples 9 to 27 and Comparative Examples 8 to 13>

1) Polymer for Blood Separating Agent (Meth)acrylic acid ester polymer (Polymer 3; manufactured by Toagosei Co., Ltd., Mw: 7600)

2) Inorganic Powder

A hydrophilic silica (AEROSIL 90G manufactured by Nippon Aerosil Co., Ltd., particle size: approx. 20 nm, specific surface area: approx. 90 m$^2$/g) was used as the inorganic powder.

3) Polyalkylene Glycol

Polyoxyethylene-polyoxypropylene glycol (NEWPOL PE-71 manufactured by Sanyo Chemical Industries, Ltd., Mn: 2300, HLB value: 3) was used as the polyalkylene glycol.

4) Polymerization Inhibitor

Materials used as polymerization inhibitors are shown in Table 5 below.

TABLE 5

| | | | Solubility (25° C.) |
|---|---|---|---|
| Material 1 | Polymerization | p-methoxyphenol | 4 g/100 ml |
| Material 2 | inhibitor | 2,5-di-t-butylhydroquinone | 0.002 g/100 ml |
| Material 3 | | phenothiazine | insoluble |
| Material 4 | | hydroquinone | 7 g/100 mL |

<Preparation of Blood Separating Agent>

EXAMPLE 9

A blood separating agent was prepared by making a formulation containing 96.399% by weight of (meth)acrylic acid ester polymer (manufactured by Toagosei Co., Ltd., Mw: 7600), 2.6% by weight of AEROSIL 90G (manufactured by Nippon Aerosil Co., Ltd.), 1% by weight of polyalkylene glycol (NEWPOL PE-71 (manufactured by Sanyo Chemical Industries, Ltd.)), and 0.001% by weight of p-methoxyphenol as a polymerization inhibitor, followed by mixing with stirring at room temperature for 10 minutes using a planetary mixer.

EXAMPLES 10 TO 14

Blood separating agents were prepared in the same manner as in Example 9, except that the mixture ratio between the polymerization inhibitor and the (meth)acrylic acid ester-based polymer was varied as shown in Table 6.

EXAMPLES 15 TO 20

Blood separating agents were prepared in the same manner as in Example 9, except that the polymerization inhibitor was changed to 2,5-di-t-butylhydroquinone and the mixture ratio between the polymerization inhibitor and the (meth)acrylic acid ester-based polymer was varied as shown in Table 6.

EXAMPLES 21 TO 26

Blood separating agents were prepared in the same manner as in Example 9, except that the polymerization inhibitor was changed to phenothiazine and the mixture ratio between the polymerization inhibitor and the (meth)acrylic acid ester-based polymer was varied as shown in Table 6.

EXAMPLE 27

A blood separating agent was prepared in the same manner as in Example 9, except that no polymerization inhibitor was added and the content of (meth)acrylic acid ester-based polymer was 96.4% by weight.

COMPARATIVE EXAMPLES 8 TO 10

Blood separating agents were prepared in the same manner as in Example 9, except that the polymerization inhibitor was changed to hydroquinone and the mixture ratio between the polymerization inhibitor and the (meth)acrylic acid ester-based polymer was varied as shown in Table 6.

COMPARATIVE EXAMPLE 11

A blood separating agent was prepared in the same manner as in Example 9, except that the amount of polymerization inhibitor p-methoxyphenol added was 6.0% by weight, the content of (meth)acrylic acid ester-based polymer was 90.4% by weight, and the materials were mixed with stirring at room temperature for three hours using a planetary mixer.

COMPARATIVE EXAMPLE 12

A blood separating agent was prepared in the same manner as in Comparative Example 11, except that the polymerization inhibitor was changed to 2,5-di-t-butylhydroquinone.

COMPARATIVE EXAMPLE 13

A blood separating agent was prepared in the same manner as in Comparative Example 11, except that the polymerization inhibitor was changed to phenothiazine.

<Preparation of Blood Collection Container>

Twenty 7-mL polyethylene terephthalate-made test tubes (13 mm diameter by 100 mm length) were prepared and each of the blood separating agents was contained in the twenty test tubes, 0.9 g per test tube, to prepare blood collection containers. The blood collection containers were exposed to γ radiation to reach a dose of 30 kGy and then evaluated in various items.

<Evaluations>

The initial blood separating agents in the blood collection containers after being exposed to γ radiation in the above manner and the initial blood collection containers were subjected to an accelerated test corresponding to the degree of storage at 25° C. for one year. Specifically, they were preserved for four weeks under conditions of 45° C. and a relative humidity of 75%. Samples of the blood separating agents before the above accelerated test, i.e., in an initial condition, and samples thereof after the accelerated test were evaluated in the following manners.

1. Measurement of Viscosity at 25° C.

The blood separating agents in an initial condition and after the accelerated test were measured in terms of viscosity at 25° C. with a rheometer DV-III (manufactured by Brookfield Engineering Laboratories, Inc.). The results are shown as "After accelerated test/initial condition" viscosity ratios.

2. Effects on Test Values

Human pooled serum was added to the prepared initial blood collection containers and let stand at 4° C. for 48 hours to obtain analytes, and the analytes were measured in 32 biochemical items. More specifically, the analytes were measured in terms of total protein, albumin, A/G ratio, total bilirubin, direct bilirubin, AST, ALT, alkaline phosphatase, leucine aminopeptidase, lactate dehydrogenase, cholinesterase, γ-GTP, CK, amylase, urea nitrogen, uric acid, creatinine, phospholipid, triglyceride, total cholesterol, HDL-cholesterol, LDL-cholesterol, β-lipoprotein, sodium, chloride, potassium, calcium, inorganic phosphorus, magnesium, iron, total iron binding capacity, and unsaturated iron binding capacity. A blood collection container to which no blood separating agent was added was used as a control to measure it in the above 32 biochemical items in the same manner. When in the cases of use of the above blood separating agents the differences of all the values measured in the above 32 biochemical items from those measured in the same items under conditions of the control were within the range of below 5%, this result is indicated by a circle sign. When in the above cases at least one of the values measured in the above items was different within the range of 5% to 10% from that of the control, this result is indicated by a triangle sign. When in the above cases at least one of the values measured in the above items was different within the range of above 10% from that of the control, this result is indicated by a cross sign. These results are indicated in Table 6.

25° C. enabled the blood separating agents to be further increased in performance stability without having any effect on the test values.

EXAMPLES 28 TO 42

(Materials Used in Examples 28 to 42)
1) Polymer for Blood Separating Agent
The polymer for the blood separating agents used was (Meth)acrylic acid ester polymer (Polymer 3; manufactured by Toagosei Co., Ltd., Mw: 7600).
2) Inorganic Powder
The inorganic powder used was a mixture of a hydrophilic silica (AEROSIL 200 manufactured by Nippon Aerosil Co., Ltd., particle size: approx. 12 nm, specific surface area: approx. 200 $m^2/g$) and a hydrophobic silica (AEROSIL R974 manufactured by Nippon Aerosil Co., Ltd., particle size:

TABLE 6

|  | Polymerization Inhibitor Type | % by weight | (Meth)acrylic Acid Ester-Based Polymer % by weight | 25° C. Viscosity Ratio After accelerated test/ initial condition | Test Values Initial |
|---|---|---|---|---|---|
| Ex. 9 | p-methoxyphenol | 0.001 | 96.399 | 1.17 | ○ |
| Ex. 10 |  | 0.005 | 96.395 | 1.13 | ○ |
| Ex. 11 |  | 0.05 | 96.35 | 1.12 | ○ |
| Ex. 12 |  | 0.5 | 95.9 | 1.1 | ○ |
| Ex. 13 |  | 3 | 93.4 | 1.1 | ○ |
| Ex. 14 |  | 5 | 91.4 | 1.05 | ○ |
| Ex. 15 | 2,5-di-t-butylhydroquinone | 0.001 | 96.399 | 1.19 | ○ |
| Ex. 16 |  | 0.005 | 96.395 | 1.1 | ○ |
| Ex. 17 |  | 0.05 | 96.35 | 1.02 | ○ |
| Ex. 18 |  | 0.5 | 95.9 | 1.04 | ○ |
| Ex. 19 |  | 3 | 93.4 | 1.04 | ○ |
| Ex. 20 |  | 5 | 91.4 | 1.06 | ○ |
| Ex. 21 | phenothiazine | 0.001 | 96.399 | 1.15 | ○ |
| Ex. 22 |  | 0.005 | 96.395 | 1.08 | ○ |
| Ex. 23 |  | 0.05 | 96.35 | 1.06 | ○ |
| Ex. 24 |  | 0.5 | 95.9 | 1.06 | ○ |
| Ex. 25 |  | 3 | 93.4 | 1.05 | ○ |
| Ex. 26 |  | 5 | 91.4 | 1.06 | ○ |
| Ex. 27 | not added | 0 | 96.4 | 1.32 | ○ |
| Comp. Ex. 8 | hydroquinone | 0.001 | 96.399 | 1.15 | x |
| Comp. Ex. 9 |  | 0.05 | 96.35 | 1.1 | x |
| Comp. Ex. 10 |  | 5 | 91.4 | 1.08 | x |

In the blood separating agents of Examples 9 to 26 in which were used the polymerization inhibitors having a solubility of 4 g/100 mL or below at 25° C., the increase in viscosity of the blood separating agents after the accelerated test was reduced as compared with Example 27 to which no polymerization inhibitor was added. In addition, no effect on the test values due to elution of the polymerization inhibitors into the serum analytes was found.

On the other hand, in Comparative Examples 8 to 10 in which was used hydroquinone having a solubility of 7 g/100 mL at 25° C., the increase in viscosity was reduced, but the effects on the test values in terms of uric acid, phospholipid, triglyceride, HDL-cholesterol, and LDL-cholesterol were found and there was also found a tendency to increase the differences in these test values from the control with increasing hydroquinone concentration. This can be considered to be due to the elution of hydroquinone into the serum analytes.

Furthermore, in Comparative Examples 11 to 13 in which the amount of polymerization inhibitor added was large, the polymerization inhibitors remained in the form of granular aggregates in the blood separating agents without being fully dispersed therein even after mixing with stirring for three hours using the planetary mixer.

As can be seen from the above, the use of the polymerization inhibitors having a solubility of 4 g/100 mL or below at approx. 12 nm, specific surface area: approx. 170 $m^2/g$, which was made hydrophobic by chemically treating the surfaces with $CH_3$ groups).
3) Polyalkylene Glycol
The polyalkylene glycol used was a mixture of polyoxyethylene-polyoxypropylene glycol (NEWPOL PE-71 manufactured by Sanyo Chemical Industries, Ltd., Mn: 2300, HLB value: 3) and polyoxypropylene glyceryl ether (PREMINOL S3011 manufactured by Asahi Glass Co., Ltd. (Enhancer 1)).
4) Polymerization Inhibitor
The polymerization inhibitor used was 0.1% by weight of 2,5-di-t-butylhydroquinone.
<Preparation of Blood Separating Agent>

EXAMPLE 28

A blood separating agent was prepared by making a formulation containing 96.35% by weight of (meth)acrylic acid ester polymer (Polymer 3; manufactured by Toagosei Co., Ltd., Mw: 7600), 1.03% by weight of 200CF (manufactured by Nippon Aerosil Co., Ltd.), 1.52% by weight of R974 (manufactured by Nippon Aerosil Co., Ltd.), 0.1% by weight of NEWPOL PE-71 (manufactured by Sanyo Chemical Industries, Ltd.), 0.9% by weight of PREMINOL S3011

(manufactured by Asahi Glass Co., Ltd.), and 0.1% by weight of 2,5-di-t-butylhydroquinone, followed by mixing with stirring at room temperature for 10 minutes using a planetary mixer.

EXAMPLES 29 TO 34

Blood separating agents were prepared in the same manner as in Example 28, except that the mixed amount of NEWPOL PE-71 (manufactured by Sanyo Chemical Industries, Ltd.) and PREMINOL S3011 (manufactured by Asahi Glass Co., Ltd.) was varied as shown in Table 7 below.

EXAMPLES 35 TO 42

Blood separating agents were prepared in the same manner as in Example 30, except that the mixed amount of 200CF (manufactured by Nippon Aerosil Co., Ltd.) and R974 (manufactured by Nippon Aerosil Co., Ltd.) was varied as shown in Table 7 below.

<Preparation Of Blood Collection Container>

Fifty 7-mL polyethylene terephthalate-made test tubes (13 mm diameter by 100 mm length) were prepared and each of the blood separating agents was contained in the fifty test tubes, 0.9 g per test tube, to prepare blood collection containers. The blood collection containers were exposed toy radiation to reach a dose of 30 kGy and then evaluated in various items.

<Evaluations>

The initial blood separating agents in the blood collection containers and the initial blood collection containers were, after being exposed to γ radiation in the above manner, subjected to an accelerated test corresponding to the degree of storage at 25° C. for one year. Specifically, they were preserved for four weeks under conditions of 45° C. and a relative humidity of 75%. Samples of the blood separating agents before the above accelerated test, i.e., in an initial condition, and samples thereof after the accelerated test were evaluated in the following manner.

1) Fluidity Evaluation of Blood Separating Agent

The fluidity evaluation of the blood separating agents was made in the same manner as in Examples 1 to 8. The results are shown in Table 7 below.

2) Evaluation of Formation State of Partition Wall

The evaluation of the formation states of the partition walls were made in the same manner as in Examples 1 to 8. The results are shown in Table 7 below.

3) Effects on Test Values

The effects on the test values were evaluated in the same manner as in the evaluation of effects on the test values performed for Examples 9 to 27. The results are shown in Table 7 below.

TABLE 7

| | Formulation | | | | | | | | Evaluation Results | | | | |
|---|---|---|---|---|---|---|---|---|---|---|---|---|---|
| | Polymer for Blood Separating Agent | | Inorganic Fine Powder | | Polyalkylene Glycol | | Polymerization Inhibitor | | Fluidity (1100 g × 5 min./15° C.) | | Formation State of Partition Wall | | Test Values Initial |
| | Type | % by weight | Type | % by weight | Type | % by weight | Type | % by weight | Initial | After accelerated test | Initial | After accelerated test | |
| Ex. 28 | Polymer 3 | 96.35% | 200CF/ R974 | 1.03%/1.52% | PE-71/ S3011 | 0.1%/0.9% | 2,5-di-t-butyl-hydroquinone | 0.10% | ○ | ○ | ○ | ○ | ○ |
| Ex. 29 | | 96.35% | | | | 0.25%/0.75% | | | ○ | ○ | ○ | ○ | ○ |
| Ex. 30 | | 96.35% | | | | 0.25%/0.5% | | | ○ | ○ | ○ | ○ | ○ |
| Ex. 31 | | 96.35% | | | | 0.5%/0.25% | | | ○ | ○ | ○ | ○ | ○ |
| Ex. 32 | | 96.60% | | | | 0.75%/0.25% | | | ○ | ○ | ○ | ○ | ○ |
| Ex. 33 | | 96.60% | | | | 0.9%/0.10% | | | ○ | ○ | ○ | ○ | ○ |
| Ex. 34 | | 97.15% | | | | 0.1%/0.1% | | | ○ | ○ | ○ | ○ | ○ |
| Ex. 35 | | 96.45% | | 1.09%/1.61% | | 0.25%/0.5% | | | ○ | ○ | ○ | ○ | ○ |
| Ex. 36 | | 96.15% | | 1.21%/1.79% | | | | | ○ | ○ | ○ | ○ | ○ |
| Ex. 37 | | 96.60% | | 1.13%/1.42% | | | | | ○ | ○ | ○ | ○ | ○ |
| Ex. 38 | | 96.45% | | 1.20%/1.50% | | | | | ○ | ○ | ○ | ○ | ○ |
| Ex. 39 | | 96.15% | | 1.33%/1.67% | | | | | ○ | ○ | ○ | ○ | ○ |
| Ex. 40 | | 96.60% | | 1.28%/1.28% | | | | | ○ | ○ | ○ | ○ | ○ |
| Ex. 41 | | 96.45% | | 1.35%/1.35% | | | | | ○ | ○ | ○ | ○ | ○ |
| Ex. 42 | | 96.15% | | 1.50%/1.50% | | | | | ○ | ○ | ○ | ○ | ○ |

As is evident from Table 7, Examples 28 to 42, in which the mixed amount of inorganic fine powder and polyalkylene glycol and the mixture ratio between them were varied, exhibited good results in terms of all of the fluidity, the formation state of partition wall, and the test values even after the accelerated test.

The invention claimed is:

1. A blood separating, agent containing:
    a (meth)acrylic acid ester-based polymer having a viscosity of 10 to 200 Pa·s at 25° C. and a ratio of viscosity at 15° C. to viscosity at 25° C. of below 4.6;
    an inorganic powder; and
    a polyalkylene glycol having a number average molecular weight of 700 or more, wherein the polyalkylene glycol is mixed at a concentration of 5% by weight or less of the total weight of the blood separating agent.

2. The blood separating agent according to claim 1, wherein the blood separating agent further contains a polymerization inhibitor having a solubility in water of 4 g/100 mL or below at 25° C.

3. The blood separating agent according to claim 1 wherein the (meth)acrylic acid ester-based polymer is a copolymer comprising a (meth)acrylic acid ester monomer and a monomer other than any (meth)acrylic acid ester monomer.

4. The blood separating agent according to claim 3, wherein the monomer other than any (meth)acrylic acid ester monomer is an aromatic vinyl monomer.

5. The blood separating agent according to claim 4, wherein the aromatic vinyl, monomer is styrene or α-methylstyrene.

6. The blood separating agent according to claim 1, wherein the polyalkylene glycol is a polymer composed of one or more monomers selected from $C_2$ to $C_4$ alkylene oxide monomers and/or a polymer composed of one or more monomers selected from $C_3$ and $C_4$ alkylene oxide monomers.

7. The blood separating agent according to claim 1, wherein the inorganic powder comprises an inorganic powder having a hydrophilic particle surface, an inorganic powder having a hydrophobic particle surface, or both.

8. A blood collection container comprising: a centrifugable cylindrical container body; and the blood separating agent according to claim 1 contained in the container body.

9. The blood separating agent according to claim 1, wherein the blood separating agent further contains a polymerization inhibitor having a solubility in water of 4 g/100 mL or below at 25° C., wherein the (meth)acrylic acid ester-based polymer is a copolymer comprising a (meth)acrylic acid ester monomer and a monomer other than any (meth)acrylic acid ester monomer, and wherein the monomer other than any (meth)acrylic acid ester monomer is an aromatic vinyl monomer.

10. The blood separating agent according to claim 1, wherein the blood separating agent further contains a polymerization inhibitor having a solubility in water of 4 g/100 mL or below at 25° C., and wherein the polyalkylene glycol is a polymer composed of one or more monomers selected from C2 to C4 alkylene oxide monomers and/or as polymer composed of one or more monomers selected from C3 and C4 alkylene oxide monomers.

11. The blood separating agent according to claim 1 wherein the (meth)acrylic acid ester-based polymer is a copolymer comprising a (meth)acrylic acid ester monomer and a monomer other than any (meth)acrylic acid ester monomer, wherein the monomer other than any (meth)acrylic acid ester monomer is an aromatic vinyl monomer, and wherein the polyalkylene glycol is a polymer composed of one or more monomers selected from C2 to C4 alkylene oxide monomers and/or a polymer composed of one or more monomers selected from C3 and C4 alkylene oxide monomers.

12. The blood separating agent according to claim 1, wherein the blood separating agent further contains a polymerization inhibitor having a solubility in water of 4 g/100 mL or below at 25° C., wherein the (meth)acrylic acid ester-based polymer is a copolymer comprising a (meth)acrylic acid ester monomer and a monomer other than any (meth)acrylic acid ester monomer, wherein the monomer other than any (meth)acrylic acid ester monomer is an aromatic vinyl monomer, and wherein the polyalkylene glycol is a polymer composed of one or more monomers selected from C2 to C4 alkylene oxide monomers and/or a polymer composed of one or more monomers selected from C3 and C4 alkylene oxide monomers.

* * * * *